(12) United States Patent
Oomen et al.

(10) Patent No.: US 11,491,292 B2
(45) Date of Patent: Nov. 8, 2022

(54) SEDATION DEVICE

(71) Applicant: Sedana Medical Limited, Naas (IE)

(72) Inventors: Glen Oomen, Naas (IE); Ron Farrell, Naas (IE); Pauric Carey, Carbury (IE)

(73) Assignee: Sedana Medical Limited, Naas (IE)

( * ) Notice: Subject to any disclaimer, the term of this patent is extended or adjusted under 35 U.S.C. 154(b) by 693 days.

(21) Appl. No.: 16/338,535

(22) PCT Filed: Oct. 2, 2017

(86) PCT No.: PCT/EP2017/075014
§ 371 (c)(1),
(2) Date: Apr. 1, 2019

(87) PCT Pub. No.: WO2017/220698
PCT Pub. Date: Dec. 28, 2017

(65) Prior Publication Data
US 2019/0247601 A1 Aug. 15, 2019
US 2019/0366026 A9 Dec. 5, 2019

Related U.S. Application Data

(63) Continuation-in-part of application No. 16/311,305, filed as application No. PCT/EP2017/065318 on Jun. 21, 2017.

(30) Foreign Application Priority Data

Jun. 21, 2016 (EP) ..................................... 16175577
Sep. 30, 2016 (EP) ..................................... 16191980

(51) Int. Cl.
*A61M 16/00* (2006.01)
*A61M 16/01* (2006.01)
(Continued)

(52) U.S. Cl.
CPC .......... *A61M 16/01* (2013.01); *A61M 16/105* (2013.01); *A61M 16/1045* (2013.01);
(Continued)

(58) Field of Classification Search
CPC ...... A61M 11/00; A61M 11/04; A61M 16/00; A61M 16/01; A61M 16/0833;
(Continued)

(56) References Cited

U.S. PATENT DOCUMENTS 4,422,939 A 12/1983 Sharp et al.
4,693,853 A 9/1987 Falb et al.
(Continued)

FOREIGN PATENT DOCUMENTS

EP 0965372 A2 12/1999
EP 0972534 A2 1/2000
(Continued)

OTHER PUBLICATIONS

Secur2005, https://www.youtube.com/watch?v=R0syXscHD94, published Jan. 17, 2007 (Year: 2007).*
(Continued)

*Primary Examiner* — Justine R Yu
*Assistant Examiner* — Matthew R Moon
(74) *Attorney, Agent, or Firm* — Michael Crilly, Esquire

(57) ABSTRACT

A sedation device (1) has a housing (2) having a ventilator chamber (3) and an associated patient chamber (4) in communication with the ventilator chamber (3). A filter (5) is mounted between the ventilator chamber (3) and the patient chamber (4) and forms a common gas-permeable dividing wall between the ventilator chamber (3) and the patient chamber (4). An inlet port (6) is provided on the ventilator chamber (3) for connection via a Y-piece to a ventilator. An outlet port (9) of the patient chamber (4) connects via a patient breathing tube (10) with a patient. An
(Continued)

associated pair of inserts are provided, namely a first insert (14) fixedly mounted in the ventilator chamber (3) and a second insert (15) fixedly mounted in the patient chamber (4). One or both of these inserts (14, 15) are mounted within the housing (2) to vary the internal volume of the housing (2) as required to suit different patients. The inserts (14, 15) are nestably engageable with an inner wall of the housing (2).

16 Claims, 8 Drawing Sheets

(51) Int. Cl.
*A61M 16/10* (2006.01)
*A61M 16/16* (2006.01)
*A61M 11/04* (2006.01)

(52) U.S. Cl.
CPC ............ *A61M 11/04* (2013.01); *A61M 16/104* (2013.01); *A61M 16/109* (2014.02); *A61M 16/161* (2014.02); *A61M 2205/7518* (2013.01)

(58) Field of Classification Search
CPC ................ A61M 16/10; A61M 16/104; A61M 16/1045; A61M 16/105; A61M 16/107; A61M 16/109; A61M 16/161; A61M 2205/0238; A61M 2205/584; A61M 2205/7509; A61M 2205/7518; A61M 2205/7536
See application file for complete search history.

(56) References Cited

U.S. PATENT DOCUMENTS

| | | | |
|---|---|---|---|
| 5,044,361 A | 9/1991 | Werner et al. | |
| 5,195,527 A * | 3/1993 | Hicks ................ | A61M 16/0833 128/204.17 |
| 5,337,739 A | 8/1994 | Lehman | |
| 5,460,172 A | 10/1995 | Eckerbom et al. | |
| 5,468,451 A | 11/1995 | Gedeon | |
| 5,970,210 A * | 10/1999 | Anthony ............. | A61M 16/142 392/386 |
| 6,152,133 A | 11/2000 | Psaros et al. | |
| 6,155,255 A | 12/2000 | Lambert | |
| 6,168,718 B1 | 1/2001 | Sutter et al. | |
| 6,206,002 B1 | 3/2001 | Lambert | |
| 6,275,650 B1 | 8/2001 | Lambert | |
| 6,363,930 B1 | 4/2002 | Clawson et al. | |
| 6,488,028 B1 | 12/2002 | Lambert | |
| 7,841,339 B2 | 11/2010 | Lambert | |
| 8,485,187 B2 | 7/2013 | Orr et al. | |
| 2004/0149281 A1 * | 8/2004 | Ahl ................... | A61M 16/1065 128/203.12 |
| 2005/0166917 A1 | 8/2005 | Ahlmen et al. | |
| 2007/0079827 A1 | 4/2007 | Lambert | |
| 2009/0050148 A1 | 2/2009 | Heinonen et al. | |
| 2009/0301475 A1 | 12/2009 | Korneff | |
| 2010/0212668 A1 | 8/2010 | Flanagan et al. | |
| 2010/0269828 A1 | 10/2010 | Orr et al. | |

FOREIGN PATENT DOCUMENTS

| | | |
|---|---|---|
| EP | 1613383 B1 | 10/2008 |
| EP | 1778324 B1 | 10/2009 |
| WO | 88/07876 A1 | 10/1988 |
| WO | 97/14465 A1 | 4/1997 |
| WO | 97/36628 A1 | 10/1997 |
| WO | 98/20926 A1 | 5/1998 |
| WO | 99/33523 A1 | 7/1999 |
| WO | 00/02610 A1 | 1/2000 |
| WO | 00/21595 A1 | 4/2000 |
| WO | 2004/087244 A1 | 10/2004 |
| WO | 2004087244 A1 | 10/2004 |
| WO | 2004/098688 A1 | 11/2004 |
| WO | 2005/037357 A1 | 4/2005 |
| WO | 2010/096299 A1 | 8/2010 |

OTHER PUBLICATIONS

International Search Report for PCT/EP2017/065318 by the European Patent Office, dated Aug. 8, 2017, 3 pages.
Written Opinion for PCT/EP2017/065318 by the European Patent Office, 5 pages.
International Search Report for PCT/EP2017/075014 by the European Patent Office; dated Nov. 29, 2017; 5 pages.
Written Opinion for PCT/EP2017/075014 by the European Patent Office; 6 pages.
Berton, Jerome MD; Sargentini, Cyril MD; Nguyen, Jean-Luc MD; Belii, Adrian MD; and Beydon, Laurent; AnaConDa Reflection Filter: Bench and Patient Evaluation of Safety and Volatile Anesthetic Conservation, Anesthesia & Analgesia: Jan. 2007—vol. 104—Issue 1—p. 130-134 doi: 10.1213/01.ane.0000248221.44383.43.

* cited by examiner

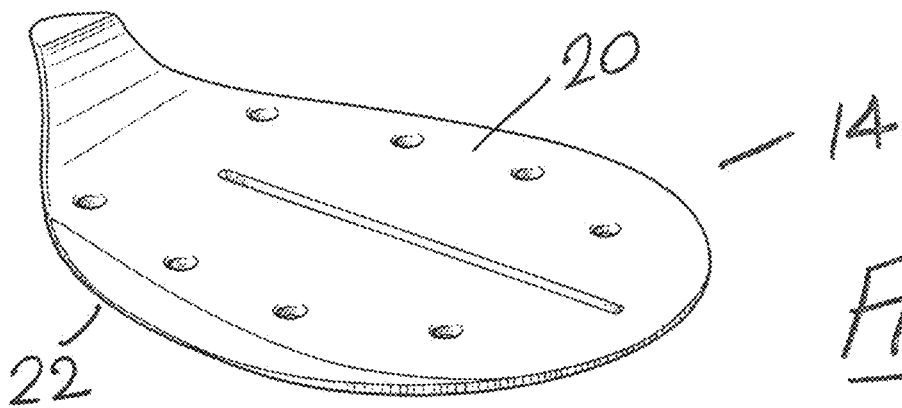
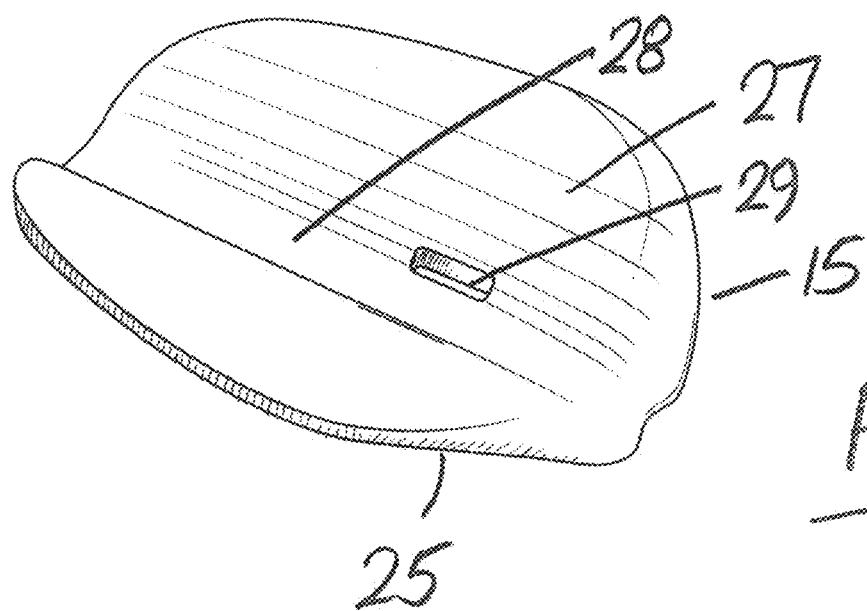

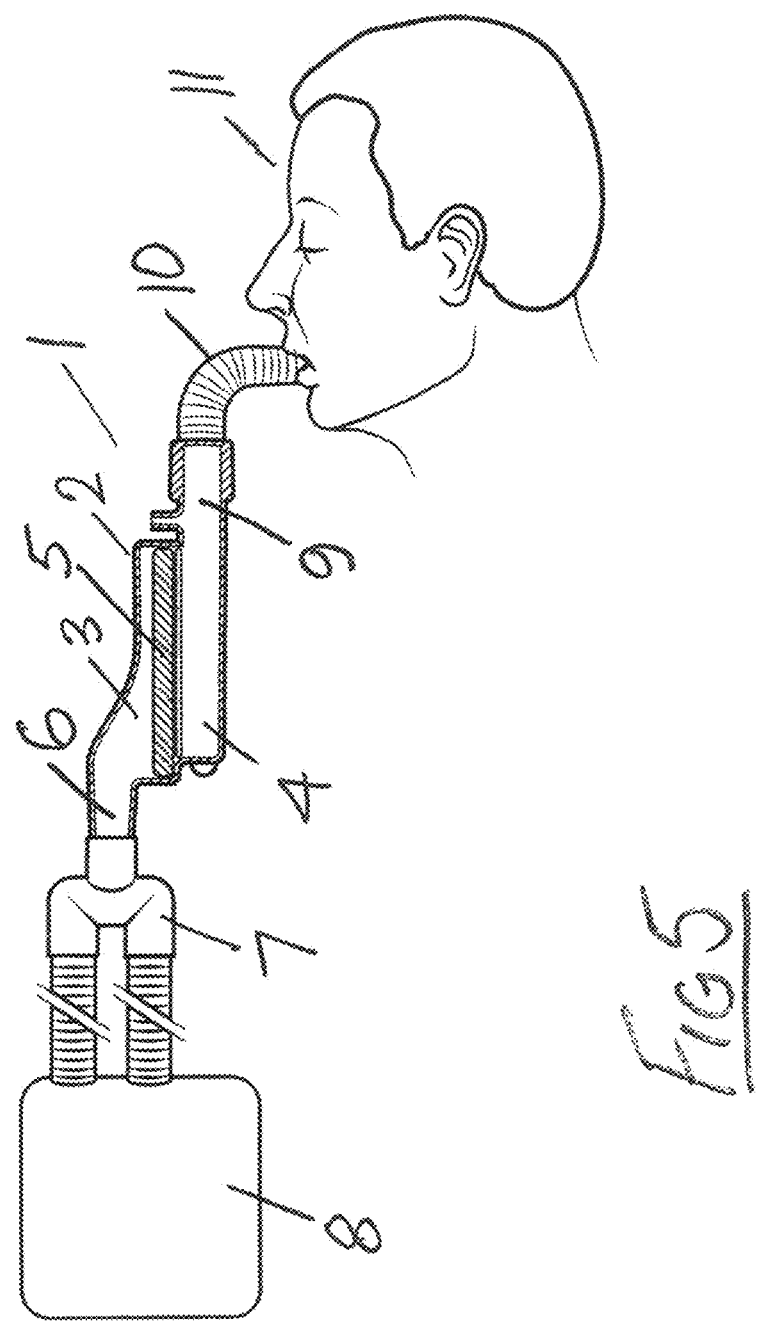

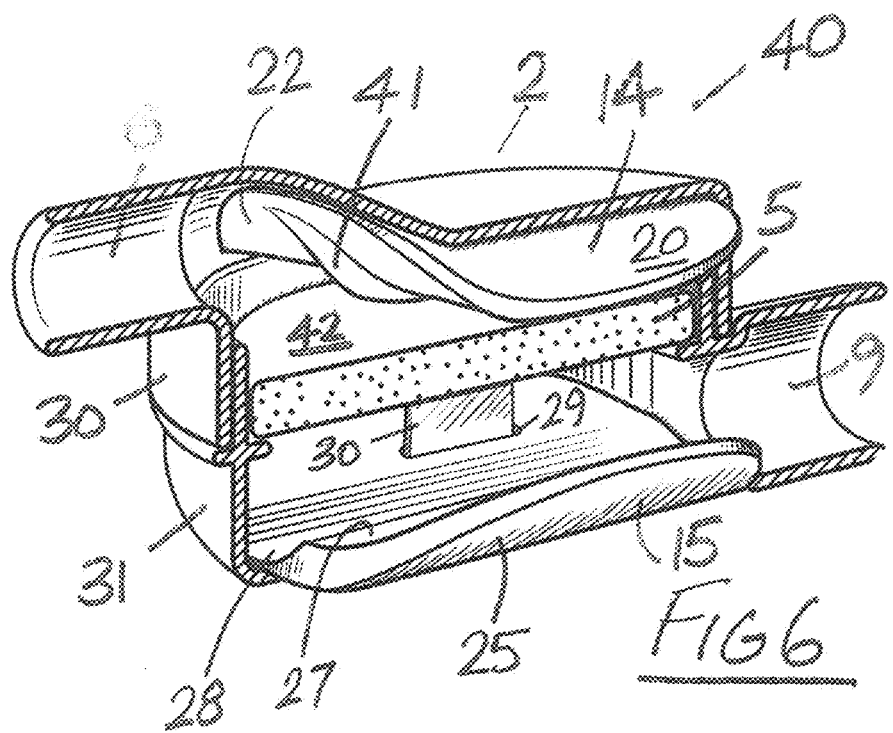
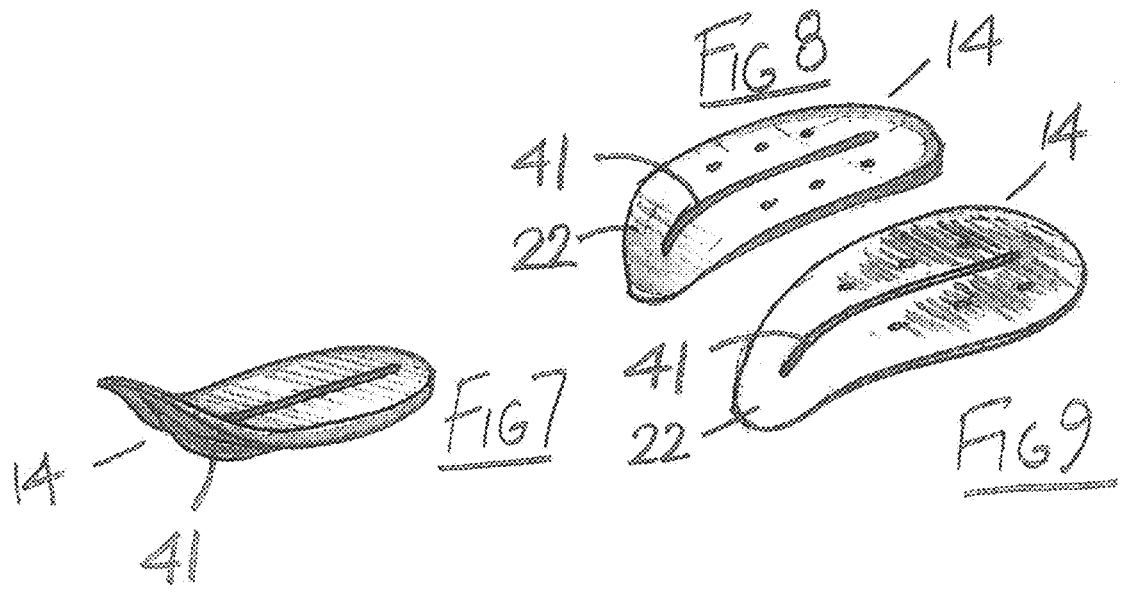

SEDATION DEVICE

CROSS REFERENCE TO RELATED APPLICATIONS

This application is a national phase to PCT Application No. PCT/EP2017/075014 filed Oct. 2, 2017 entitled A Sedation Device, which in turn claims priority to European Patent Application No. EP16191980.8 filed Sep. 30, 2016 entitled A Humidity and Moisture Exchange Device.

This national phase is also a continuation-in-part to U.S. patent application Ser. No. 16/311,305 filed Dec. 19, 2018 entitled Sedation Device which is a national phase to PCT Application No. PCT/EP2017/065318 filed Jun. 21, 2017 entitled A Sedation Device, which in turn claims priority to European Patent Application No. EP16175577.2 filed Jun. 21, 2016 entitled A Sedation Device.

The subject matters of all prior applications are incorporated in their entirety herein by reference thereto.

FEDERALLY SPONSORED RESEARCH AND DEVELOPMENT

None.

BACKGROUND OF THE INVENTION

1. Field of the Invention

This invention relates to a sedation device for volatile anaesthetic delivery to a patient.

2. Background

The invention particularly relates to a sedation device comprising a housing, an interior volume of the housing defining a housing deadspace volume, the housing having a ventilator chamber and an associated juxtaposed patient chamber communicating with the ventilator chamber, a filter mounted between the ventilator chamber and the patient chamber forming a common gas-permeable dividing wall between the ventilator chamber and the patient chamber, the ventilator chamber and the patient chamber communicating through the filter, the ventilator chamber having an inlet port for connection to a ventilator, the patient chamber having an outlet port for connection to a patient breathing tube, and an evaporator mounted within the patient chamber for delivery of a volatile sedative into the patient chamber.

The sedation device in use is mounted between a ventilator and a patient. Typically the ventilator sends fresh air to a patient through a tube or hose and exhaled air is exhausted back to the mechanical ventilator through a second hose. A Y-piece placed between the ventilator and patient separates the two hoses: the first hose carrying incoming fresh air flow from the ventilator; and the second hose, carrying exhaled $CO_2$ and moisture laden air to the ventilator. The sedation device is mounted between the Y-piece and the patient to deliver a volatile sedative into the air stream. To prevent aerosolized pathogens from being exhaled by the patient and contaminating the ventilator machine, a filter is incorporated in the sedation device mounted between the patient and the Y-piece. In addition to capturing particulate material and pathogens, filters of different media can also serve to retain the moisture exhaled by the patient and, during the inhalation phase of the cycle, return the moisture to the patient. Different absorbent or reflective media can be used in the filter to reflect additional exhalants, such as volatile anaesthetics or sedatives, back to the patient.

$CO_2$ rich air will always be exhaled into the ventilator circuit between the patient and the Y-piece. This volume of breathed air not involved in gas exchange is called the "deadspace". The larger the volume of this deadspace, the more exhaled $CO_2$ rich air may reside in it. How high the concentration of $CO_2$ becomes in a given volume of deadspace is dependent upon the tidal volume of the patient. For example, a patient with a deep, large tidal volume will flush much more of the $CO_2$ laden air from the deadspace with each breathing cycle than will a patient, such as a child, with a low tidal volume, taking small, shallow breaths. Unable to completely flush this space on the exhale, the smaller patient with a smaller tidal volume will quickly increase the concentration of the $CO_2$ in the breathing gas with each breathing cycle. It should be noted that the body does have a natural deadspace. This natural deadspace is the trachea or airway between lungs and mouth or nose, so there is always some natural rebreathing.

Increasing the concentration of $CO_2$ in the deadspace, however, can have severe consequences for the patient. The $CO_2$ concentration in the rebreathed or exhaled air can be considered in equilibrium with the $CO_2$ dissolved in the patient's blood. Therefore, in having too small a tidal volume or too great a deadspace and failing to adequately clear the $CO_2$ from it, the patient's blood $CO_2$ will rise accordingly, creating a state of respiratory acidosis in the patient. As the chemoreceptors and respiratory nuclei of the brain only respond to blood $CO_2$ concentrations, the normal physiological reflex to increasing blood $CO_2$ is increasing respiratory rate and depth to clear it. When this cannot happen or cannot happen naturally, as in a ventilated patient, the patient undergoes a very dangerous condition of respiratory stress. It should be noted that completely eliminating the deadspace is also undesirable. Decreasing the $CO_2$ concentration in the rebreathed air forces the respiratory nuclei of the brain to depress natural respiratory rates and tidal volume to maintain homeostasis.

In reducing deadspace, simply making the components of the circuit, such as the sedation device or an endotracheal tube, smaller is challenging. Doing so will typically increase the resistance of the air flowing through the components from inlet to outlet. This resistance creates a pressure gradient across the component, called pressure drop, making it particularly difficult for the patient to exhale quickly enough before receiving the next breath from the ventilator. The ventilation rate must be subsequently slowed to allow enough exhalation. There is risk that the compensating low ventilation rate will not permit sufficient oxygen to reach the patient.

Simply reducing the size of the sedation device reduces the size of the filter and this adversely affects the reflection rate of heat, moisture and volatile sedative. While the filter could be enlarged in the direction of air flow through the device to compensate for the reduction in filter cross-sectional area due to size reduction, this will increase the pressure drop across the filter which is undesirable for the patient.

From a manufacturing point of view producing separate sedation devices in a number of sizes, with different deadspace volumes suitable for different sized patients, for example adults of different lung capacity and children, is relatively expensive as different tooling, moulds, filters, etc. are required for each different size of sedation device.

The present invention is directed towards overcoming these problems.

SUMMARY OF THE INVENTION

According to the invention there is provided a sedation device including a housing, an interior volume of the housing defining a housing deadspace volume, the housing having a ventilator chamber and an associated juxtaposed patient chamber communicating with the ventilator chamber, a filter mounted between the ventilator chamber and the patient chamber forming a common gas-permeable inner dividing wall between the ventilator chamber and the patient chamber, the ventilator chamber and the patient chamber communicating through the filter, the ventilator chamber having an inlet port for connection to a ventilator, the inlet port positioned at a side of the housing to promote air flow across a surface of the filter, the patient chamber having an outlet port for connection to a patient breathing tube, the outlet portion positioned at a side of the housing to promote air flow across a surface of the filter, an evaporator mounted within the patient chamber, characterised in that at least one insert is fixedly mounted within the housing to reduce the deadspace volume within the housing, the or each insert being mounted against an outer wall of the ventilator chamber, or against an outer wall of the patient chamber spaced-apart from the filter to provide an air flow path therebetween. Advantageously as the device provides the ability to vary the internal deadspace volume of the housing of the sedation device during manufacture, it can be easily adapted for use with persons of different lung capacity, for example adults and children, for optimum treatment of the patient. Conveniently, from a manufacturing and a cost point of view, the device also makes it unnecessary to provide a range of housings in different sizes to accommodate different patients. Also, the insert could provide additional functions within the sedation device, such as delivery of drug, or the sensing of a drug or patient metabolite.

In another embodiment of the invention the insert nests with the outer wall of the ventilator chamber or the outer wall of the patient chamber, an outer face of the insert being shaped for complementary interengagement with an inner face of the associated outer wall.

In another embodiment of the invention the insert has an inner face shaped to facilitate air flow through the housing.

In another embodiment of the invention a multi-part insert is provided with said insert parts being fixedly mounted in one or both of the ventilator chamber and the patient chamber.

In another embodiment of the invention the insert has means to vary the volume of the insert.

In another embodiment of the invention the insert is expandable between a collapsed position and an expanded position.

In another embodiment of the invention the insert incorporates one of more sensors for sensing one or more parameters of air delivered through the housing.

In another embodiment of the invention a first insert is provided for mounting in the ventilator chamber and a second insert is provided for mounting in the patient chamber.

In another embodiment of the invention the insert comprises a drug-eluting insert.

In another embodiment of the invention the insert is nestable with an inner face of the outer wall of the ventilator chamber and a central air distribution fin is mounted on an inner face of the insert projecting outwardly therefrom in alignment with the inlet port.

In another embodiment of the invention the insert is adapted to provide a colour change indication when exposed over time to exhaled pharmacological, metabolic or pathogenic agents to indicate the presence of a pathogen, or an undesirable concentration of a chemical. The colour change indication may be due to a time related change of colour to indicate the device has been in use for a preset period and is depleted.

In another embodiment of the invention the insert incorporates a nebulizer, or a nebulizer is mounted thereon.

In another embodiment of the invention the insert incorporates a humidifier, or a humidifier is mounted thereon.

In another embodiment of the invention the insert is for mounting in the patient chamber and has a central slot aligned with the outlet port for reception of the evaporator mounted in the patient chamber.

In another embodiment of the invention the insert incorporates means for mounting an evaporator thereon.

In another embodiment of the invention the insert is for mounting the patient chamber and the insert incorporates an evaporator.

In another embodiment of the invention the insert is for mounting in the patient chamber and comprises a plurality of vanes projecting inwardly from an inner face of the insert.

In another embodiment of the invention the vanes are porous to facilitate delivery of a volatile material through the vanes into the patient chamber.

In another aspect the invention provides a method for manufacturing a sedation device of the invention wherein the method includes the step of mounting and fixing at least one insert within the housing to reduce the internal deadspace volume of the housing to a selected desirable internal deadspace volume.

BRIEF DESCRIPTION OF THE DRAWINGS

The invention will be more clearly understood by the following description of some embodiments thereof, given by way of example only with reference to the accompanying drawings.

FIG. 3 is a perspective view of an insert portion of the device.

FIG. 4 is a perspective view of another insert portion of the device.

FIG. 5 is a schematic illustration of a sedation device in use.

FIG. 6 is a sectional perspective view of another sedation device according to the invention.

FIG. 7 is a perspective view of an insert forming portion of the device of FIG. 6.

FIG. 8 is a perspective view showing an underside of the insert of FIG. 7.

FIG. 9 is a view similar to FIG. 8 showing the insert in another condition of use

DETAILED DESCRIPTION OF THE INVENTION

Figure 1:
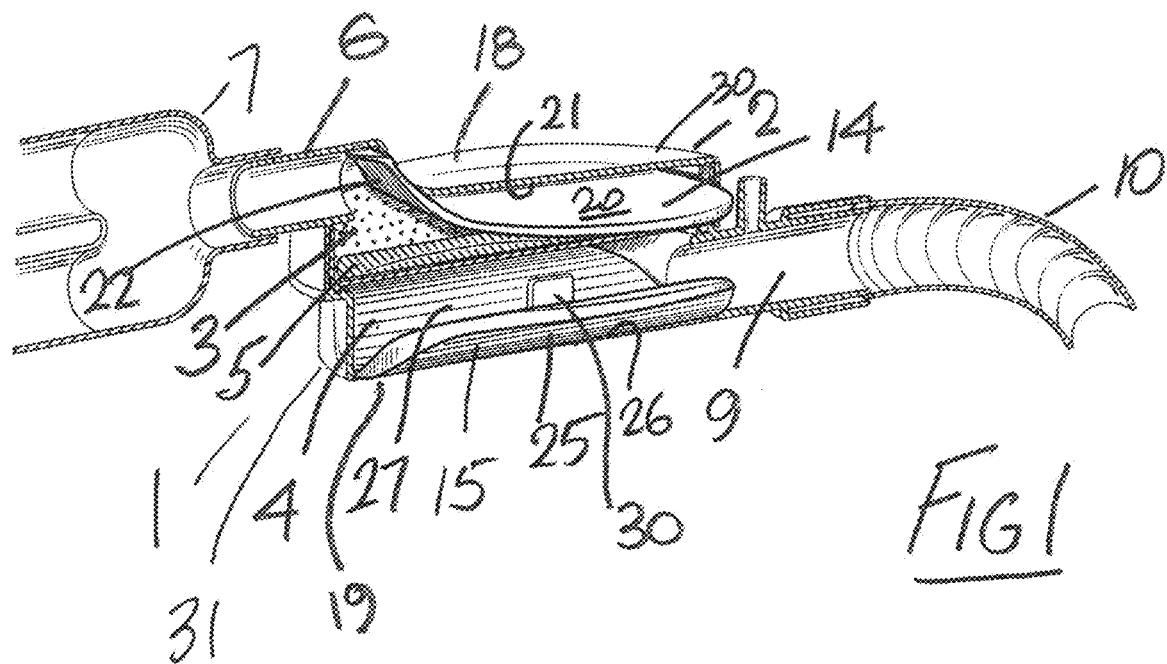
FIG. 1 is a sectional perspective view of a sedation device according to the invention.
Figure 2:
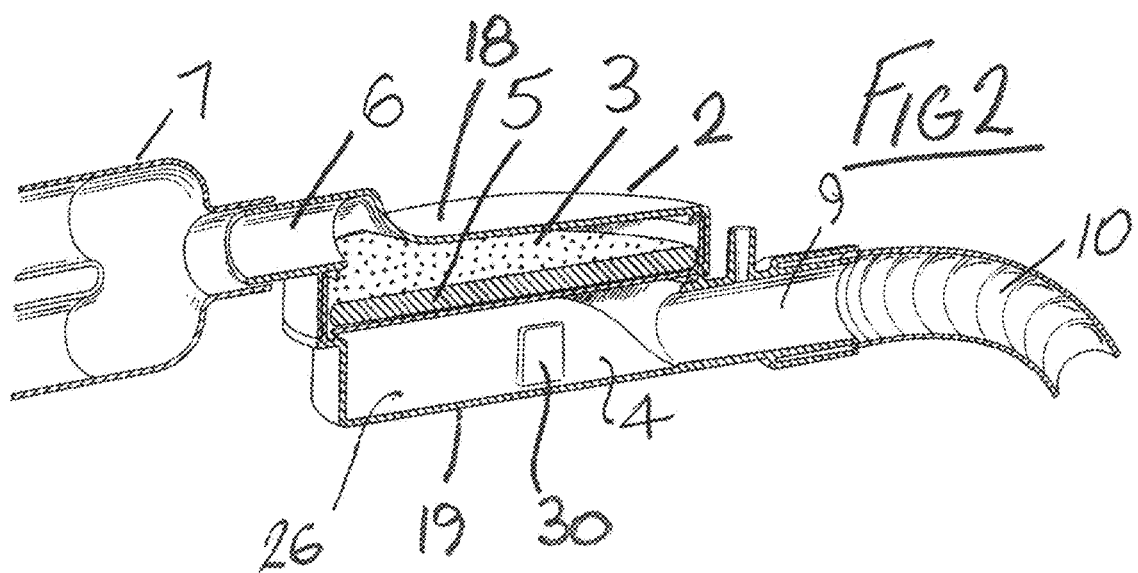
FIG. 2 is a view similar to FIG. 1 showing a housing portion of the device.

Referring to the drawings, and initially FIGS. 1 to 5 thereof, there is illustrated a sedation device according to the invention indicated generally by the reference numeral 1.

The sedation device 1 comprises a housing 2 having a ventilator chamber 3 and an associated patient chamber 4 in communication with the ventilator chamber 3. A filter 5 is mounted between the ventilator chamber 3 and the patient chamber 4 and forms a common gas-permeable inner dividing wall between the ventilator chamber 3 and the patient chamber 4. An inlet port 6 is provided on the ventilator chamber 3 for connection via a Y-piece 7 to a ventilator 8 (FIG. 5). An outlet port 9 of the patient chamber 4 connects via a patient breathing tube 10 with a patient 11 (FIG. 5). An evaporator (not shown) is mounted within the patient chamber 4 for delivery of a volatile sedative into the patient chamber 4 in use. An interior volume of the housing 2 defines a housing deadspace volume, which might for example be about 110 ml or 120 ml. In accordance with the present invention insert means is provided for varying the internal deadspace volume of the housing 2, said insert means in this case comprising an associated pair of inserts, namely a first insert 14 which is fixedly mounted in the ventilator chamber 3 and a second insert 15 which is fixedly mounted in the patient chamber 4. One or both of these inserts 14, 15 can be fixedly mounted within the housing 2 during manufacture to vary the internal deadspace volume of the housing 2 as required to suit different patients.

It will be noted that each of the inserts 14, 15 are nestably engagable with an inner face of an outer wall of the housing 2, spaced-apart from the filter 5 to provide an air flow path therebetween. An outer face 20 of the first insert 14 nestably engages against an inner face 21 at a top 18 of the outer wall of the housing 2. An inner face 22 of the first insert 14 is shaped to facilitate smooth air flow through the ventilator chamber 3 of the housing 2 across a surface of the filter 5.

Similarly, an outer face 25 of the second insert 15 is shaped for nesting engagement against an inner face 26 of a bottom 19 of the outer wall of the housing 2 within the patient chamber 4. An inner face 27 of the second insert 15 is shaped to promote smooth air flow through the patient chamber 4 of the housing 2. A central channel 28 is provided in the second insert 15 to facilitate mounting means for evaporating or nebulizing a drug within the patient chamber 4. Through-holes 29 in the insert 15 allow through passage of filter support posts 30 which project inwardly from the bottom 19 of the outer wall.

The housing 2 is provided in two interlocking parts, namely an upper part 30 forming the ventilator chamber 3 and an associated lower part 31 forming the patient chamber 4 for complementary inter-engagement to form the housing 2. These parts 30, 31 snap together and may be glued, welded or otherwise fixed together to form the housing 2.

The filter 5 comprises an absorbent carbon felt filter adjacent to an anti-microbial and anti-viral filter. The activated carbon on the filter 5 functions to reflect heat, moisture and volatile anaesthetic back to the patient. The anti-bacterial and anti-viral filter serves to protect the ventilator circuit from pathogenic contamination.

In use, the sedation device 1 can be used either with one or both of the inserts 14, 15 (as shown in FIG. 1) to provide a sedation device 1 with different internal deadspace volumes suited to different patients. For example, without the inserts 14, 15 the internal deadspace volume of the housing 2 might be about 100 ml or 110 ml, whereas by use of a suitable insert 14, 15 the internal deadspace volume of the housing 2 might be readily easily reduced to 30 ml, 50 ml or 60 ml for example, or indeed any desired internal deadspace volume in the range 30 ml to 110 ml. During manufacture of the sedation device 1 suitable inserts are selected and fixed within the housing 2 so that upon assembly of the housing 2 a desired internal housing deadspace volume is achieved. Thus conveniently a single housing 2 of maximum required deadspace volume can be produced and by securing inserts of different size within the housing 2, sedation devices 1 having a range of internal deadspace volumes can be produced.

While the inserts 14, 15 allow adjustment of the internal deadspace volume of the housing 2, at the same time they are designed to minimise flow resistance and pressure drop across the sedation device 1 when they are in use to ensure a smooth flow of air through the device 1 for patient safety and comfort. It will be noted also that the internal deadspace volume can be reduced without reducing the filter size which thus maintains a good reflection capability.

The inserts 14, 15 can be made of a material that is absorbent and reflective to augment the capacity of the filter 5 to return moisture or volatile pharmacological agents to the patient. Further, the insert 14, 15 could be used to deliver a drug to the patient through passive evaporation, active vaporisation, nebulisation, atomisation or be made of or coated or impregnated with a drug eluting material. It is also envisaged that the insert could be adapted to deliver two or more drugs.

Referring now to FIGS. 6 to 9 there is shown another sedation device according to the invention indicated generally by the reference numeral 40. Parts similar to those described previously are assigned the same reference numerals. In this case the first insert 14 is adapted to provide a change of colour indication (as shown in FIG. 9) when exposed over time to exhaled pharmacological, metabolic or pathogenic agents to indicate the presence of a pathogen, undesirable concentration of a chemical or that the device is worn and needs to be replaced. In this case also a central air distribution fin 41 is mounted on the inner face 22 of the insert 14, projecting outwardly therefrom in alignment with the inlet port 6, that is in alignment with a centre of the inlet port 6. This facilitates an even distribution of air across the upper surface 42 of the filter 5.

FIGS. 10 to 17 show various other insert designs.

Figure 10:
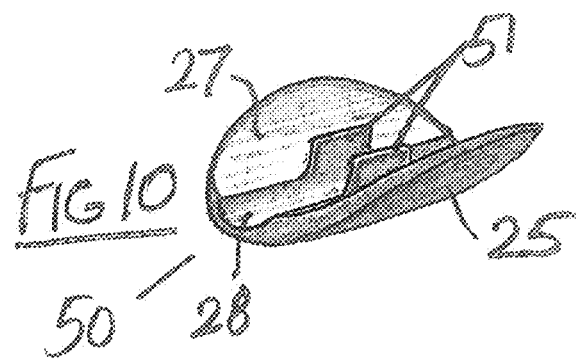
FIGS. 10-17 are various views of other insert designs according to the invention.

FIG. 10 shows another insert 50 for mounting in the patient chamber 4. Upstanding supports 51 are provided at opposite sides of the channel 28 to support the filter 5 spaced-apart from the inner face 27 to provide an air flow path between the filter 5 and the insert 50.

Figure 11A:
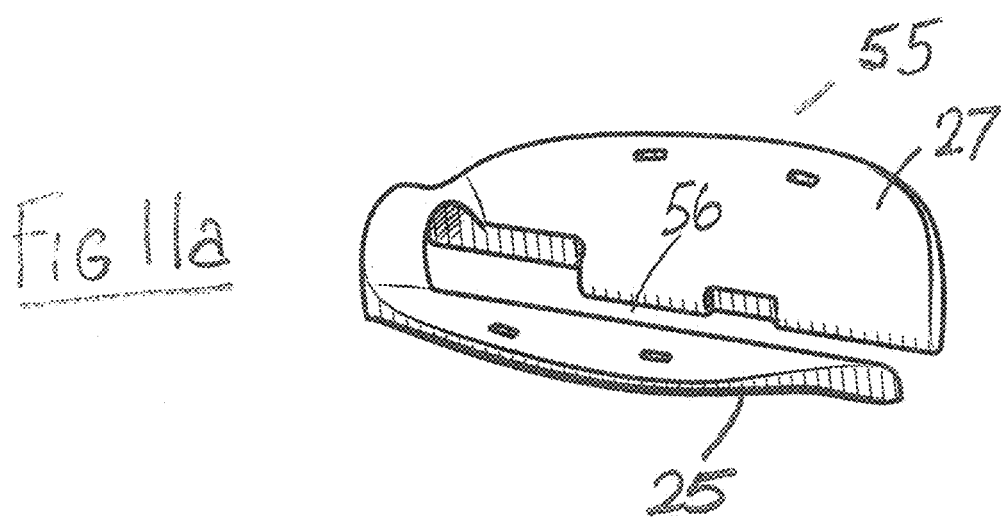
Figure 11B:
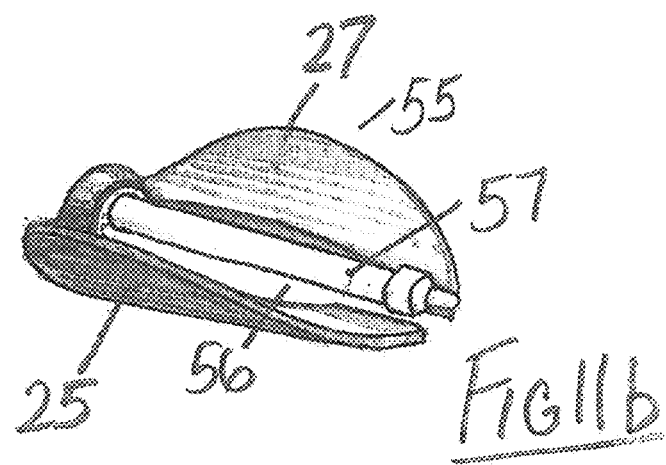

In FIG. 11 an insert 55 has a central slot 56 to accommodate an evaporator 57 when the insert 55 is mounted in the patient chamber 4. FIGS. 11a and 11b show two design options to achieve this.

Figure 12:
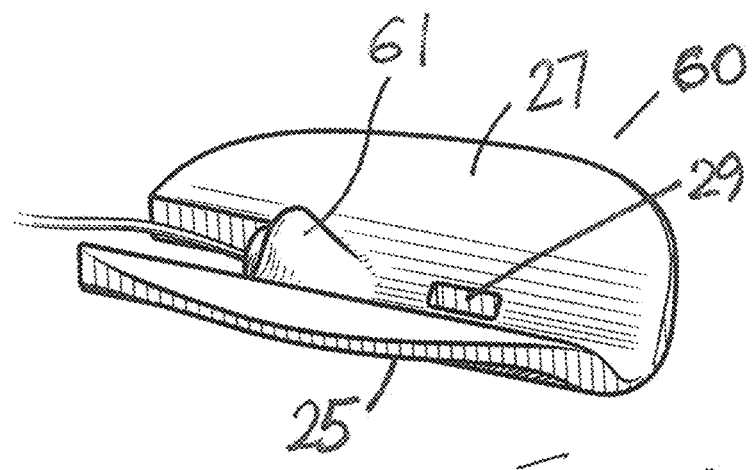

Another insert 60 is shown in FIG. 12 which in this case incorporates an evaporator. A connector 61 can be connected to an associated reservoir, of anaesthetic for example or a volatile medication, for delivery into the insert 60 and evaporation through the inner face 27 of the insert 60 into the patient chamber 4 of the device 1.

Figure 13:
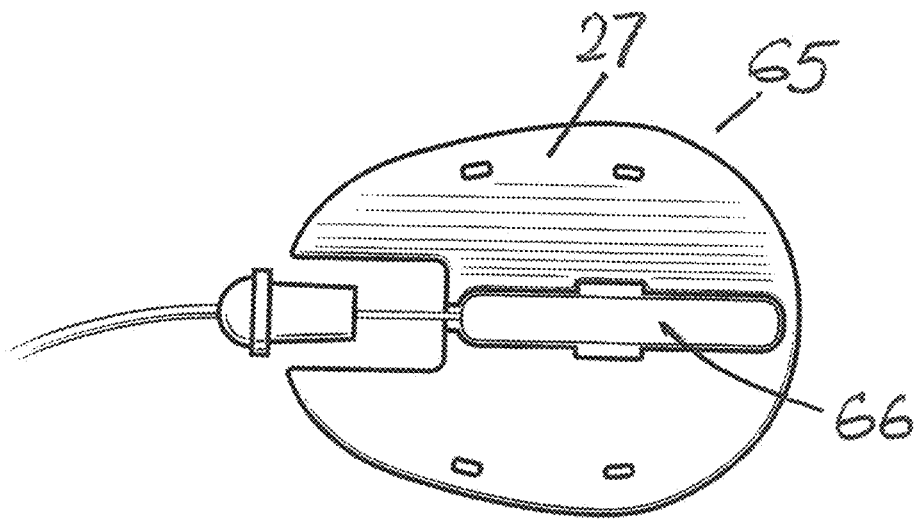

FIG. 13 shows an insert 65 which incorporates a sensor 66 to sense desired parameters such as pressure or humidity or possibly the presence of a particular chemical. Instead of the sensor 66 a vaporiser, nebulizer or humidifier could be mounted on the insert 65.

Figure 14:
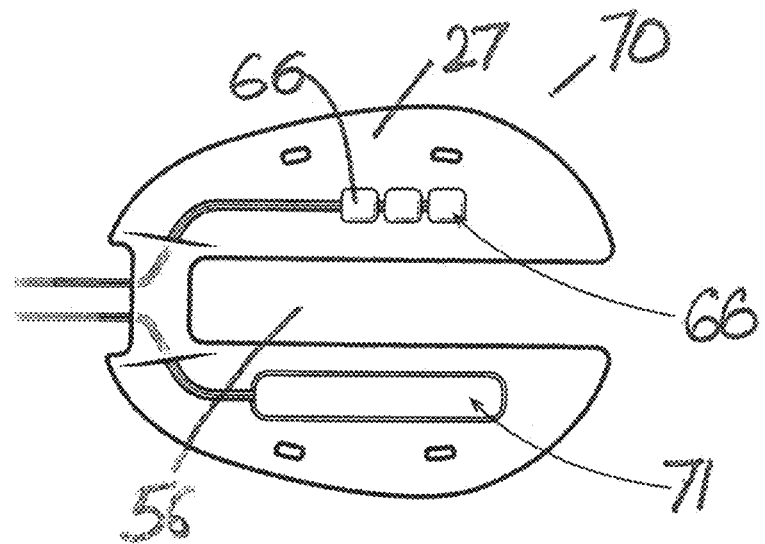

FIG. 14 shows an insert 70 similar to that shown in FIG. 11 but in this case incorporating a number of sensors 66 and a separate delivery device 71 for delivery of a volatile medication into the patient chamber 4 of the device 1.

Figure 15:
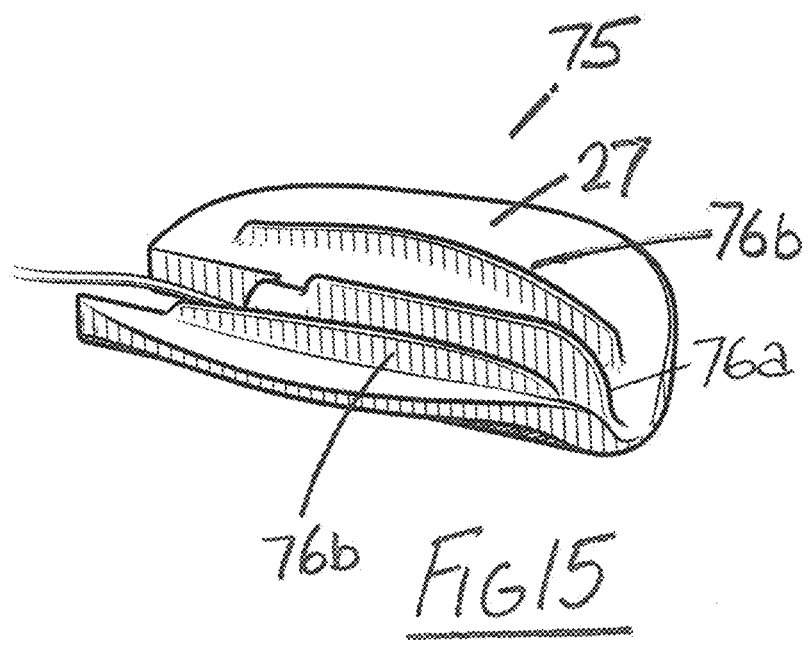

In FIG. 15 there is shown an insert 75 incorporating a number of upstanding vanes 76 which project outwardly of the inner face 27 of the insert 75 to increase the surface area for emission of volatile material into the patient chamber 4 and control the flow of air through the patient chamber 4. The vanes 76 may be substantially parallel to the outlet port 9 when the insert 75 is mounted in the patient chamber 4. That is a central vane 76*a* is centrally aligned with the outlet port 9 and outer vanes 76*b* are substantially parallel to the central vane 76*a* or curve inwardly towards the central vane 76*a* in the direction of the outlet port 9.

Figure 16:
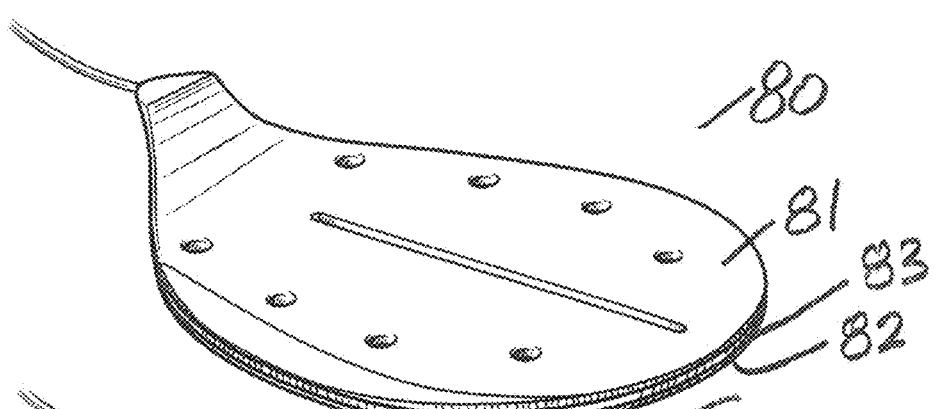
Figure 17:
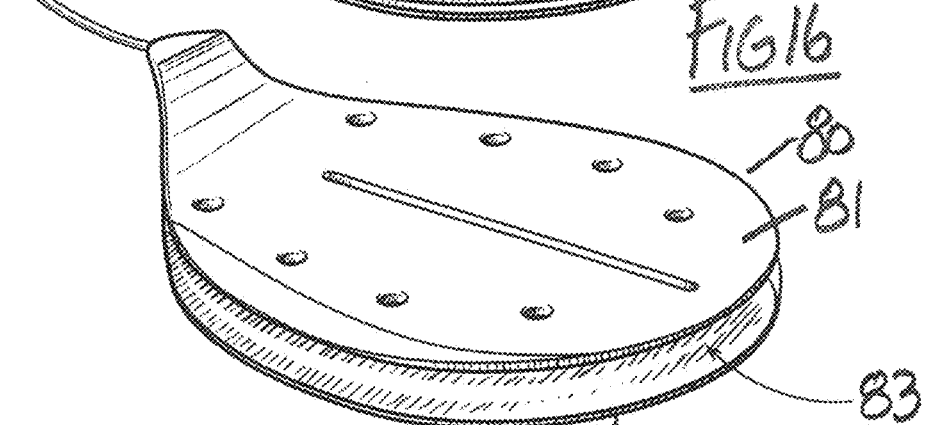

A variable volume insert 80 is shown in FIG. 16 and FIG. 17. In this case the insert 80 has upper and lower panels 81, 82 separated by an inflatable bladder or bag 83 mounted between the panels 81, 82. Inflating or deflating the bag 83 will vary the volume of the insert 80. Any suitable fluid may be used to inflate the bag 83, air generally being the most convenient.

Figure 18:
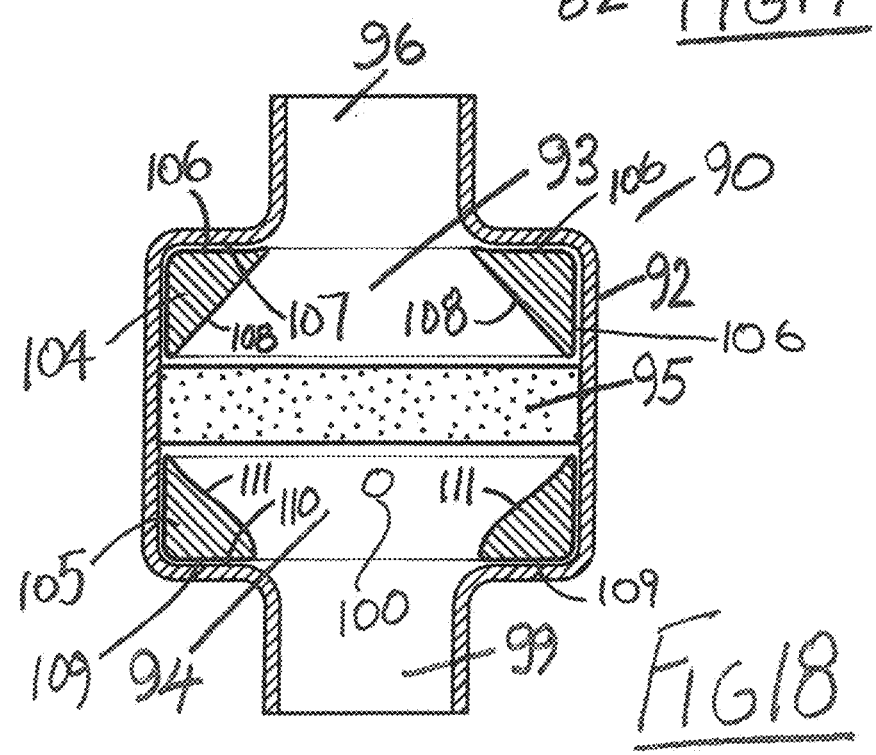
FIG. 18 is a schematic sectional elevational view of another sedation device of the invention.

Referring to FIG. 18 there is illustrated another sedation device according to the invention indicated generally by the reference numeral 90. The sedation device 90 comprises a generally cylindrical housing 92 having a ventilator chamber 93 and an associated patient chamber 94 in communication with the ventilator chamber 93. A filter 95 is mounted between the ventilator chamber 93 and the patient chamber 94 and forms a common gas-permeable dividing wall between the ventilator chamber 93 and the patient chamber 94. An inlet port 96 is provided on the ventilator chamber 93 for connection to the ventilator 8. An outlet port 99 of the patient chamber 94 connects via the patient breathing tube 10 with a patient 11. An evaporator 100 is mounted within the patient chamber 94 to deliver a volatile sedative into the patient chamber 94 in use. Air flows straight through the housing 92 between the inlet port 96, and the outlet port 99 through the filter 95. The means for varying the internal volume of the housing 92, in this case comprises an associated pair of inserts, namely a first insert 104 for mounting in the ventilator chamber 93 and a second insert 105 for mounting in the patient chamber 94. One or both of these inserts can be mounted and fixed within the housing 92 to vary the internal volume of the housing 92 as required to suit different patients. It will be noted that each of the inserts 104, 105 are nestably engagable with an inner wall of the housing 92. An outer face 106 of the first insert 104 nestably engages against an inner face 107 of the housing wall at a top of the housing 92. An inner face 108 of the first insert 104 is shaped to facilitate smooth air flow through the ventilator chamber 93 of the housing 92. In this case the inner face 108 is tapered outwardly from the inlet port 96 to the filter 95. Similarly, an outer face 109 of the second insert 105 is shaped for nesting engagement against an inner face 110 of the housing wall at a bottom of the housing 92 within the patient chamber 94. An inner face 111 of the second insert 105 is shaped to promote smooth air flow through the patient chamber 94 of the housing 92. The inner face 111 tapers outwardly from the outlet port 99 to the filter 95.

Advantageously the invention facilitates fine tuning of the deadspace volume of the sedation device to accommodate different patient requirements without needing to manufacture sedation devices in a myriad of individual volumes that might be clinically useful. The invention being proposed is a sedation device and an associated insert, or series of inserts that can be inserted into the sedation device by the manufacturer to reduce the internal volume and deadspace of that device. The invention firstly increases the range of tidal volumes over which an existing sedation device could be clinically useful without needing to manufacture a costly array of entirely unique housings and filters. Secondly, such an insert would also carefully consider how the air flows over it and through the device, and is designed to reduce resistance to keep pressure drop to a minimum.

It would also be advantageous and add value, with such an insert proposed by the invention, to increase the functionality of an existing sedation device. Additional functions could be designed into the insert to include: a means of delivering additional agents, such as volatile or aerosolized drugs; a chemical or physical sensory capability; an ability to indicate wear or use; or an ability to dynamically alter the internal volume of the sedation device.

In this specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described which may be varied in construction and detail within the scope of the appended claims.

The invention claimed is:

1. A sedation device including:
   a housing;
   an interior volume of the housing defining a housing deadspace volume, the housing having a ventilator chamber and an associated juxtaposed patient chamber communicating with the ventilator chamber;
   a filter mounted between the ventilator chamber and the patient chamber forming a common gas-permeable dividing wall between the ventilator chamber and the patient chamber, the ventilator chamber and the patient chamber communicating through the filter, the ventilator chamber having an inlet port for connection to a ventilator, the inlet port positioned at a side of the housing to promote air flow across a surface of the filter, the patient chamber having an outlet port for connection to a patient breathing tube, the outlet port positioned at a side of the housing to promote air flow across a surface of the filter; and
   an evaporator mounted within the patient chamber;
   wherein at least one insert is fixedly mounted within the housing to reduce the deadspace volume within the housing, the at least one insert being mounted against an outer wall of the ventilator chamber or against an outer wall of the patient chamber spaced-apart from the filter to provide an air flow path therebetween.

2. The sedation device as claimed in claim 1, wherein the at least one insert nests with the outer wall of the ventilator chamber or the outer wall of the patient chamber, an outer face of the at least one insert being shaped for complementary interengagement with an inner face of the associated outer wall.

3. The sedation device as claimed in claim 2, wherein the at least one insert has an inner face shaped to facilitate air flow through the housing.

4. The sedation device as claimed in 1, wherein the at least one insert is a multi-part insert with insert parts of the multi-part insert being fixedly mounted in one or both of the ventilator chamber and the patient chamber.

5. The sedation device as claimed in claim 1, wherein the at least one insert is expandable between a collapsed position and an expanded position.

6. The sedation device as claimed in claim 1, wherein the at least one insert incorporates one of more sensors for sensing one or more parameters of air delivered through the housing.

7. The sedation device as claimed in claim 1, wherein the at least one insert comprises a first insert and a second insert, the first insert is provided for mounting in the ventilator chamber and the second insert is provided for mounting in the patient chamber.

8. The sedation device as claimed in claim 1, wherein the at least one insert comprises a drug-eluting insert.

9. The sedation device as claimed in claim 1, wherein the at least one insert is nestable with an inner face of the outer wall of the ventilator chamber and a central air distribution fin is mounted on an inner face of the at least one insert projecting outwardly therefrom in alignment with the inlet port.

10. The sedation device as claimed in claim 1, wherein the at least one insert is adapted to provide a colour change indication when exposed over time to exhaled pharmacological, metabolic or pathogenic agents to indicate presence of a pathogen, or an undesirable concentration of a chemical.

11. The sedation device as claimed in claim 1, wherein the at least one insert incorporates a nebulizer.

12. The sedation device as claimed in claim 1, wherein the at least one insert incorporates a humidifier.

13. The sedation device as claimed in claim 1, wherein the at least one insert is for mounting in the patient chamber and the at least one insert has a central slot aligned with the outlet port for reception of the evaporator mounted in the patient chamber.

14. The sedation device as claimed in claim 1, wherein the at least one insert is for mounting in the patient chamber and the at least one insert incorporates an evaporator.

15. The sedation device as claimed in claim 1, wherein the at least one insert is for mounting in the patient chamber and comprises a plurality of vanes projecting inwardly from an inner face of the at least one insert.

16. The sedation device as claimed in claim 15, wherein the vanes are porous to facilitate delivery of a volatile material through the vanes into the patient chamber.

* * * * *